US006272204B1

(12) United States Patent
Amtower et al.

(10) Patent No.: US 6,272,204 B1
(45) Date of Patent: Aug. 7, 2001

(54) INTEGRATED X-RAY AND VISUAL INSPECTION SYSTEMS

(75) Inventors: Richard E. Amtower, Dana Point; Shih-Liang Chen, Yorba Linda; Jason T. McGaffey, San Juan Capistrano, all of CA (US)

(73) Assignee: CR Technology, Inc., Aliso Viejo, CA (US)

( * ) Notice: Subject to any disclaimer, the term of this patent is extended or adjusted under 35 U.S.C. 154(b) by 0 days.

(21) Appl. No.: 09/255,975

(22) Filed: Feb. 23, 1999

(51) Int. Cl.[7] .................................................. G01N 23/04
(52) U.S. Cl. .............................. 378/63; 378/58; 378/98; 378/98.3; 382/145; 382/150
(58) Field of Search ................................. 378/63, 62, 58, 378/98, 98.3; 382/145, 147, 150

(56) References Cited

U.S. PATENT DOCUMENTS

| | | | |
|---|---|---|---|
| 5,561,696 | * 10/1996 | Adams et al. | 378/62 |
| 5,754,621 | * 5/1998 | Suzuki et al. | 378/58 |
| 5,892,808 | * 4/1999 | Goulding et al. | 378/58 |
| 6,009,145 | * 12/1999 | Zweig et al. | 378/58 |

* cited by examiner

Primary Examiner—David V. Bruce
Assistant Examiner—Drew A. Dunn
(74) Attorney, Agent, or Firm—Blakely, Sokoloff, Taylor & Zafman LLP

(57) ABSTRACT

An integrated X-ray and visual inspection system having an inspection subsystem with a holder holding an object to be inspected, an X-ray source, a camera receiving an X-ray image of an object to be inspected and a camera receiving a visible image of an object to be inspected, the X-ray source and camera receiving the X-ray image being positioned on opposite sides of the holder. A display may also be provided for displaying the images. The system is well suited to the inspection of printed circuit boards having electronic components mounted thereon, in which case the holder may be a conveyor for the printed circuit boards. Independent positioning of the X-ray source and camera receiving the X-ray image allows offset images of the printed circuit board topside and bottomside features of the board. Various other features of the system and methods are disclosed.

30 Claims, 7 Drawing Sheets

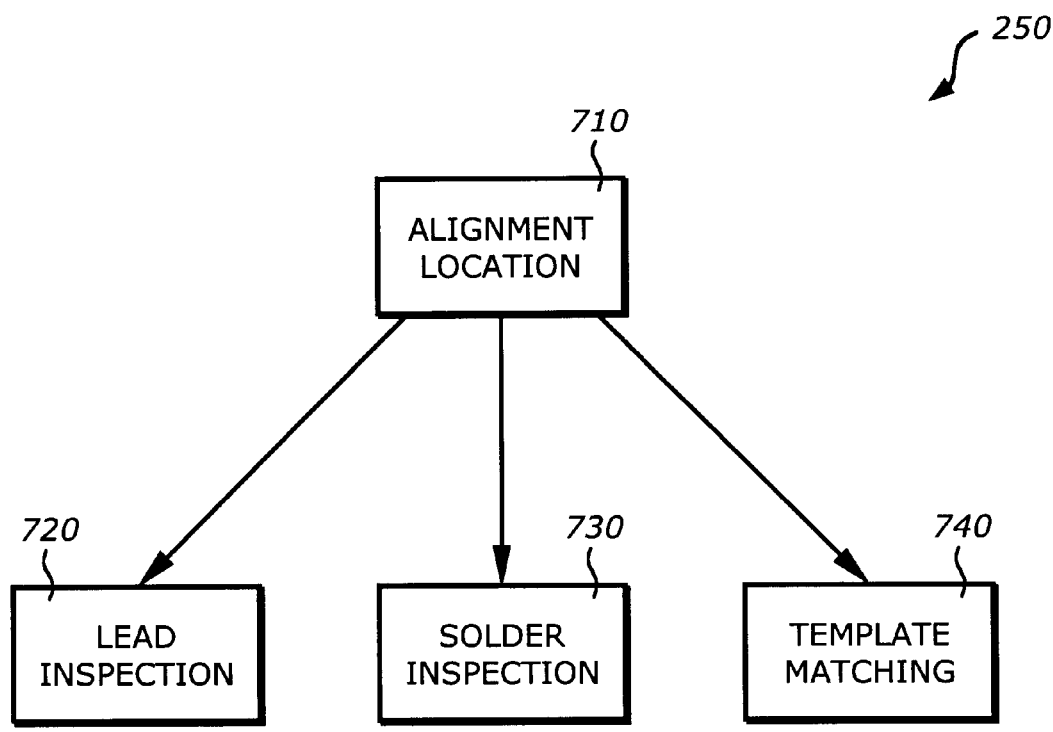

INTEGRATED X-RAY AND VISUAL INSPECTION SYSTEMS

BACKGROUND OF THE INVENTION

1. Field of the Invention

This invention relates to automated vision inspection systems. In particular, this invention relates to integrated X-ray and visual inspection systems.

2. Description of Related Art

Automatic vision inspection systems have been used in many applications such as quality control, non destructive testing, and automatic manufacturing assembly processes. The design of such inspection systems depends on the nature of the applications. One important component of a vision inspection system is the sensing element which acquires the information about the object under inspection. Typical techniques of sensing include X-ray imaging, video camera, laser, etc.

X-ray imaging involves the use of an X-ray source that provides X-ray radiation through the object. The energy of the X-rays is attenuated in the penetration path. A sensing array, e.g. photo diodes, receives the attenuated X-rays and records the absorption profile. An image is created based on this absorption profile which reflects certain characteristics on the object under inspection. Automatic techniques in image analysis are then applied to process the image to detect any abnormal conditions.

Video camera imaging is another sensing technique that acquires the image of the object under inspection. In a system utilizing a video camera sensor, a video camera or optical imaging sensing array (e.g., charge coupled device array) is mounted at an appropriate location to view the object location. The image of the object in the visual frequency range is captured and digitized.

Each of the above techniques provides different types of information on the object under inspection depending on the specific application. One example of such an industrial inspection system is the inspection of electronic components on electronic assembly boards.

Inspecting electronic components on assembly boards involves the detection of assembly defects such as missing components, irregular solder paste, bad reflow, reverse polarity, wrong components, etc. Many new packaging technologies have presented challenges to automatic inspection. One example is Ball Grid Array (BGA) technology. Defects in BGA assemblies are difficult to detect. Some examples of BGA defects are: bridging, insufficient strength (too little solder), voids (due to contamination or paste problems), opens, poor wetting, solder balls (material ejected from solder during reflow), and misregistration (ball not centered on the pad).

In X-ray inspection, the X-rays penetrate through the connection and provide density information throughout the volume of the connection. Hidden defects can be easily detected by X-ray techniques. However, visual information may not be accurately obtained by X-rays. On the other hand, a video camera provides excellent visual information such as part labels, colors, etc. but cannot provide information on hidden structures such as solder joints under a chip carrier of a component with a BGA package.

Furthermore, traditional inspection is carried out on a fixed viewing basis. Although a fixed viewing inspection is simple, it does not provide complete information on the defects. For example, certain solder joints or lead defects can only be visible clearly at a certain orientation. Inspecting these areas at a fixed viewing angle may not reveal all the defects.

Accordingly, there is a need in the technology to provide a moving inspection and combine the two methods of inspection in an integrated environment to improve the inspection quality.

SUMMARY OF THE INVENTION

An integrated X-ray and visual inspection system having an inspection subsystem with a holder holding an object to be inspected, an X-ray source, a camera receiving an X-ray image of an object to be inspected and a camera receiving a visible image of an object to be inspected, the X-ray source and camera receiving the X-ray image being positioned on opposite sides of the holder is disclosed. A display may also be provided for displaying the images. The system is well suited to the inspection of printed circuit boards having electronic components mounted thereon, in which case the holder may be a conveyor for the printed circuit boards. Independent positioning of the X-ray source and camera receiving the X-ray image allows offset images of the printed circuit board topside and bottomside features of the board. Various other features of the system and methods are disclosed, including techniques for automated inspection.

BRIEF DESCRIPTION OF THE DRAWINGS

The objects, features and advantages of the present invention will become apparent from the following detailed description of the present invention in which:

FIG. 7 is a diagram illustrating an inspection module according to one embodiment of the present invention.

FIG. 8 is a diagram illustrating a report generation module according to one embodiment of the present invention.

DESCRIPTION OF THE PRESENT INVENTION

The present invention discloses a method and apparatus for integrating X-ray and visual inspection techniques. The method provide a number of images at different viewing angles. The method combines the complementary features of the two techniques to reinforce the defect report. The result is a highly reliable system that can detect many assembly defects with minimal number of false errors.

In the following description, for purposes of explanation, numerous details are set forth in order to provide a thorough understanding of the present invention. However, it will be apparent to one skilled in the art that these specific details are not required in order to practice the present invention. In other instances, well known electrical structures and circuits are shown in block diagram form in order not to obscure the present invention.

Figure 1:
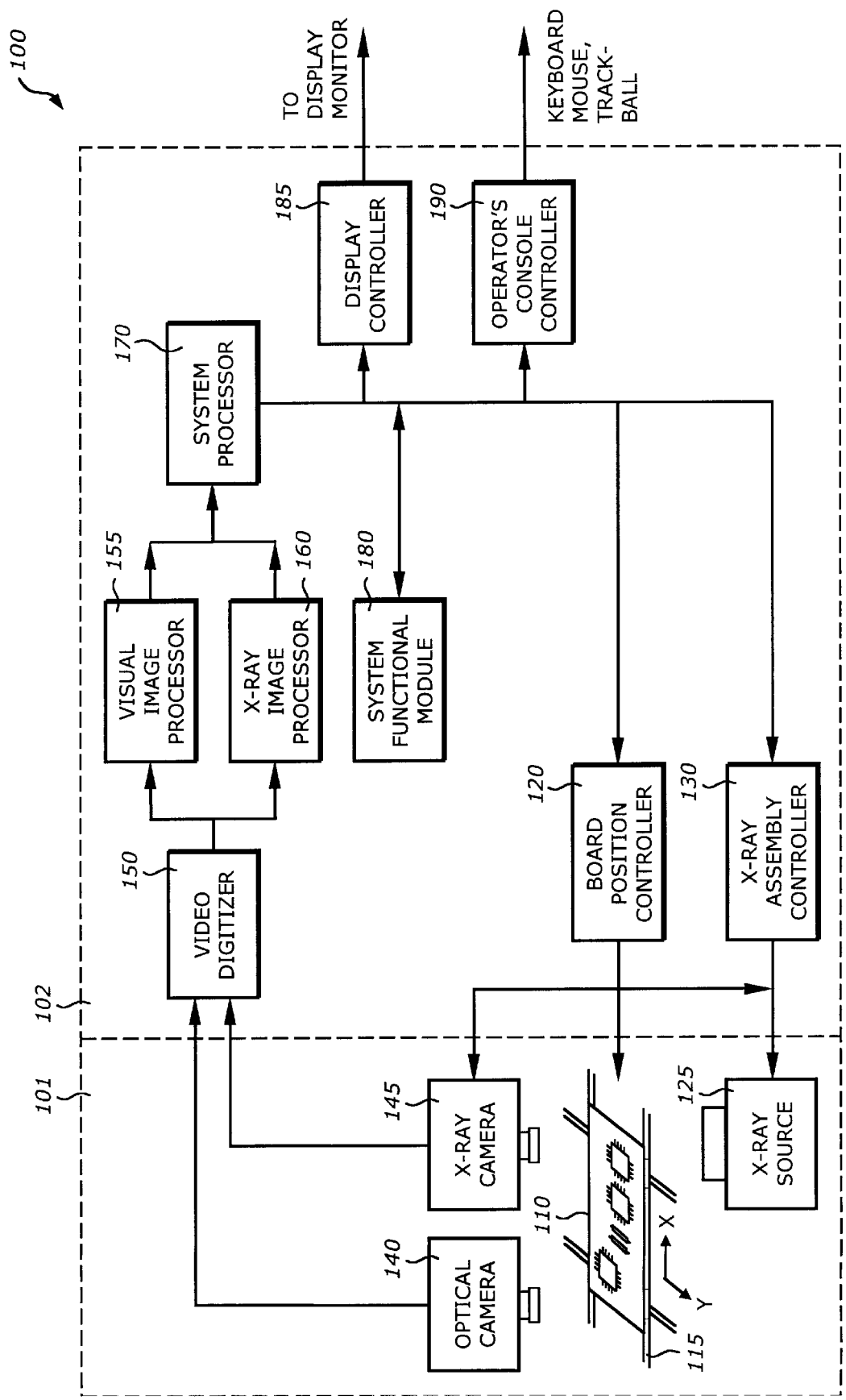
FIG. 1 is a block diagram illustration of one embodiment of a system that operates in accordance with the teachings of the present invention.

FIG. 1 is a block diagram illustration of one embodiment of a system 100 that operates in accordance with the teachings of the present invention. The system 100 includes an inspection subsystem 101 and a processing subsystem 102.

The inspection subsystem 101 houses the imaging sources, board holder, and other lighting control structures. The inspection subsystem 101 includes an object under inspection (OUI) 110, a conveyor assembly 115, an X-ray source 125, an X-ray camera 145, and an optical camera 140.

The OUI 110 is typically a printed circuit board (PCB) containing electronic components. The OUI 110 is mounted on the conveyor assembly 115 and is exposed to the X-ray radiation from the X-ray source 125. The conveyor assembly 115 is controlled by the processing subsystem 102.

The X-ray source 125 provides a highly focused X-ray beam penetrating through the OUI 110. The X-ray source may operate at an energy level ranging from 50 kV to 130 kV. The high energy provides microfocus and sharp image while the low energy provides a large spot size with low penetration power. The X-ray camera 145 receives the intensity profile of the OUI 110 as a result of the radiation from the X-ray source 125. The X-ray camera 145 generates an image which represents the intensity profile of the OUI 110.

The optical camera 140 provides a visual image of the OUI 110 as captured optically. The optical camera 140 is capable of zooming to provide a magnified image of a section of the board. In one embodiment, there are a number of video cameras with different fields of view on the board optimized for small, medium, or large components. The visual image is magnified by one of the following methods: a motorized zoom, a motorized lens change, and multiple cameras/ beamsplitters. Color inspection is also possible by using dichroic beamsplitters.

The X-ray image and the visual image generated by the X-ray camera 145 and the optical camera 140 are input to the processing unit 102. In addition, the X-ray imaging assembly including the X-ray source 125 and the X-ray camera 145 is positionable to provide image of the OUI 110 at different locations.

The processing subsystem 102 receives and processes the images from the cameras 140 and 145. The processing subsystem 102 also generates control signals to control the movement of the conveyor assembly 115, the X-ray imaging assembly which includes the X-ray source 125 and the X-ray camera 145. The processing subsystem 102 includes a board position controller, an X-ray assembly controller 130, a video digitizer 150, a visual image processor 155, an X-ray image processor 160, a system processor 170, a system module 180, a display controller 185, and an operator's console controller 190.

The board position controller 120 controls the conveyor assembly 115 when the OUI 110 is moved through the inspection area. The X-ray assembly controller 130 controls the operation and the movement of the X-ray imaging assembly. Under the control of the X-ray assembly controller 130, the X-ray camera and the associated X-ray source can be moved in both X and Y directions providing a positionable inspection of the OUI 110. The X-Y movements of the X-ray imaging assembly provide different views for the image of the OUI 110. These different views help improve the inspection quality because defects can be more fully examined and inspected.

The video digitizer 150 digitizes the video signal representing the image of the OUI 110. In one embodiment, the video digitizer 150 is a frame grabber that captures the video image, converts into digital data by an analog-to-digital converter, and stores in a buffer memory. The video digitizer 150 also has a multiplexer to select the video sources so that the image can be selected either from the optical camera 140 or the X-ray camera 145.

The visual image processor (VIP) 155 receives the visual image from the optical camera 140 and processes visual image data. The processing functions include detection of component presence and position, component identification, orientation and polarity, and solder defects.

The X-ray image processor (XIP) 160 receives the X-ray image from the X-ray camera 145 and processes the X-ray image data. The processing functions include detection of voids, solder joint quality, and wire sweep measurement.

The system processor 170 interfaces with the visual image processor 155 and the X-ray image processor 160 and integrates the two processors. In one embodiment, the system processor 170 is a computer system built around the Pentium processor manufactured by Intel. The system processor 170 sends commands to and receives processing results from the visual image processor 155 and the X-ray image processor 160. The system processor 170 performs the integrating functions to combine results from the visual image processor 155 and the X-ray image processor 160.

The system processor 170 also communicates with the board position controller 120 and the X-ray assembly controller 130 to control the operation and movement of the conveyor assembly 115 and the X-ray image assembly 125 and 145.

The system module 180 performs the main tasks of the processing unit 102. In one embodiment, the system module 180 includes programs or functions to perform user's interface, system control, imaging, training, and inspection.

The display controller 185 displays images received and/ or processed by the system processor on a video monitor. The operator's console controller 190 receives user's inputs from data entry means such as track ball, mouse, and keyboard.

Figure 2:
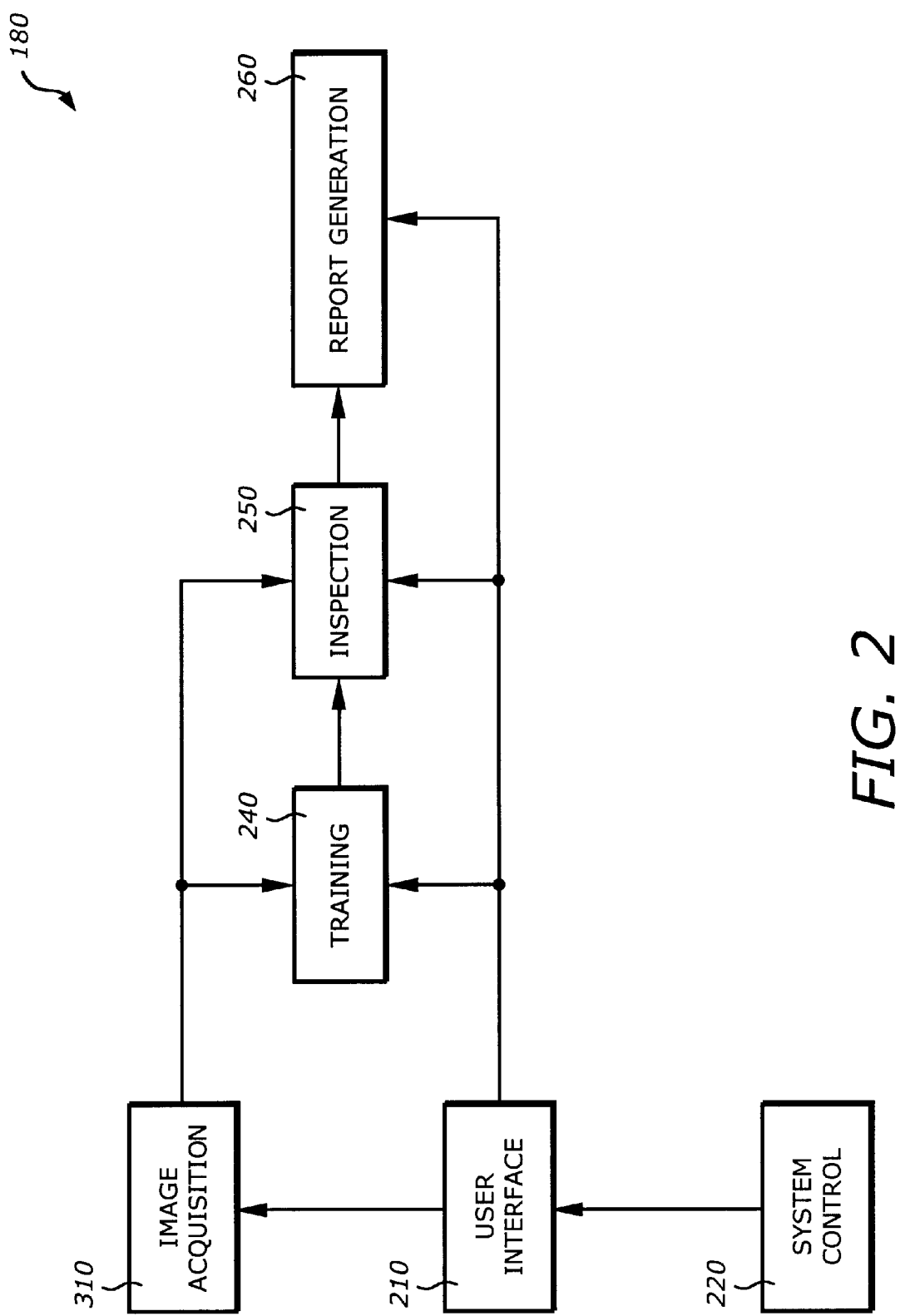
FIG. 2 is a diagram illustrating a system module according to one embodiment of the present invention.

FIG. 2 is a diagram illustrating a system module 180 according to one embodiment of the present invention. The system module 180 includes a user's interface module 210, a system control module 220, an image acquisition module 230, a training module 240, an inspection module 250, and a report generation module 260.

The user's interface module 210 receives inputs from the operator and sends the control information to the system control module 220 and the image acquisition module 230. The operator's inputs include keyboard entry, trackball movement, mouse pointing and clicking, etc. The system control module 220 receives the control information from the user's interface module 210 to control the inspection assembly. The system control module 220 performs positioning of the X-ray imaging assembly, optical camera assembly, and other mechanical functions. The image acquisition module 230 acquires the image of the object under inspection (OUI) via the optical camera 140 and the X-ray camera 145. The image acquisition module 220 receives control information the user's interface module 210.

The training module 240 performs training to prepare the system for inspection. The training module 240 receives image from known good objects or boards and generates templates in a database. The inspection module 250 performs actual inspection of the OUI 110 using information provided by the training module 240. The report generation module 260 receives the results from the inspection module 250 and generates reports of the inspection.

Figure 3:
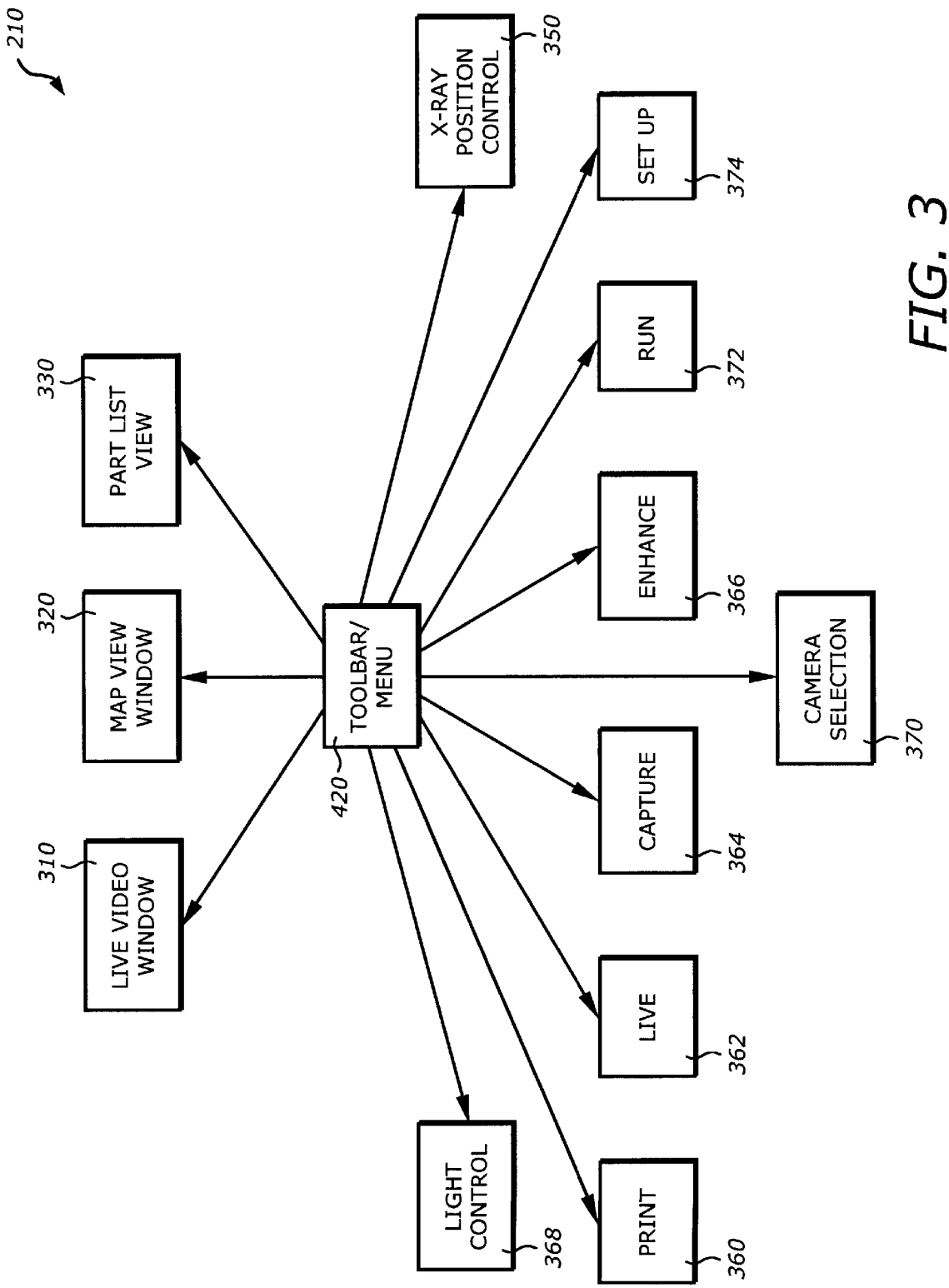
FIG. 3 is a diagram illustrating a user's interface module according to one embodiment of the present invention.

FIG. 3 is a diagram illustrating a user's interface module 210 according to one embodiment of the present invention. The user interface module 210 includes a live video window function 310, a map view window function 320, a part list view function 330, and a toolbar/menu function 340.

The live video window function 310 displays a live video image of the board in real-time. The map view window function 320 provides a global view of the entire board. The map view window function 320 also allows a platform to move the optical camera 140 and/or the X-ray imaging assembly 125 and 145. The part list view function 330 lists all the parts that have been trained on the board, the defective parts, and the parts in the library.

The toolbar/menu function 340 provides convenient user choice of actions using a menu or a set of icons. The toolbar/menu function 340 includes a number of items such as X-ray position control 350, a print item 360, a live item 362, a capture item 364, an enhance item 366, a lighting control item 368, a camera selection item 370, a run item 372, and a set-up item 374. As is known by one skilled in the art, other action items can be used according to the functionality of the system.

Figure 4:
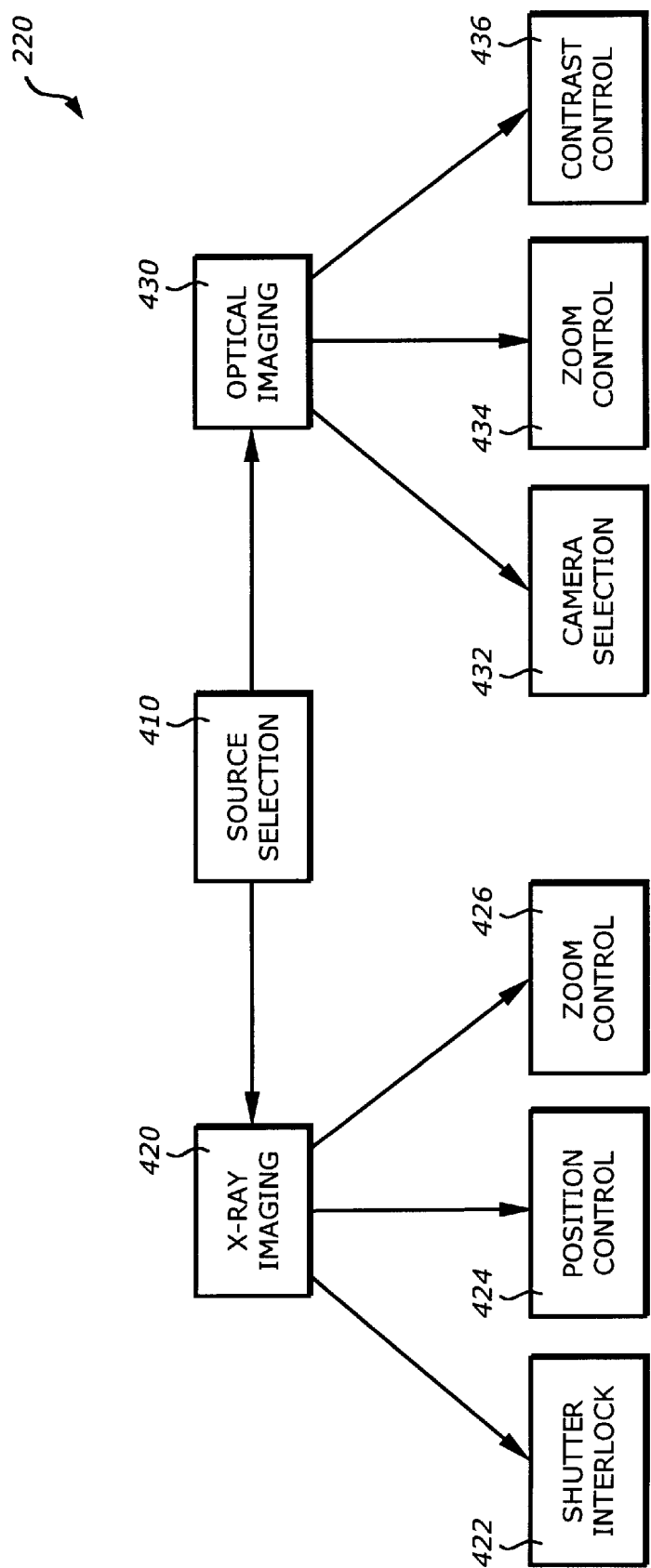
FIG. 4 is a diagram illustrating a system control module according to one embodiment of the present invention.

FIG. 4 is a diagram illustrating a system control module 220 according to one embodiment of the present invention. The system control module 220 includes a source selection function 410, an X-ray imaging control function 420, and an optical imaging control function 430.

The source selection function 410 selects the captured image between the X-ray camera 145 and the optical camera 140. The choice of the camera allows the user to tailor the sensitivity of the imaging according to the characteristics of the OUI 110.

The X-ray imaging control function 420 controls the X-ray imaging assembly which includes the X-ray camera 145 and the X-ray source 125. The X-ray imaging control function 420 is configured to perform at least a shutter interlock action 422, a position control action 424, and a zoom control action 426.

The shutter interlock action 422 turns on or off the X-ray system to provide a safety feature to the system in case X-ray radiation becomes undesirable. The position control action 424 moves the X-ray camera 145 in the X-Y directions. The use of positionable X-ray source provides offset views which allows separation of the topside and bottomside features. The zoom control action 426 allows the X-ray camera 145 to magnify the X-ray image at a selected location.

The optical imaging control function 430 controls the optical camera such as a camera selection action 432, a zoom control action 434, and a contrast control action 436. The camera selection action 432 selects a camera from a group of camera to obtain different resolutions and/or image quality. The zoom control action 434 provides image magnification for the visual images. The contrast control action 436 provides contrast to the visual image.

Figure 5:
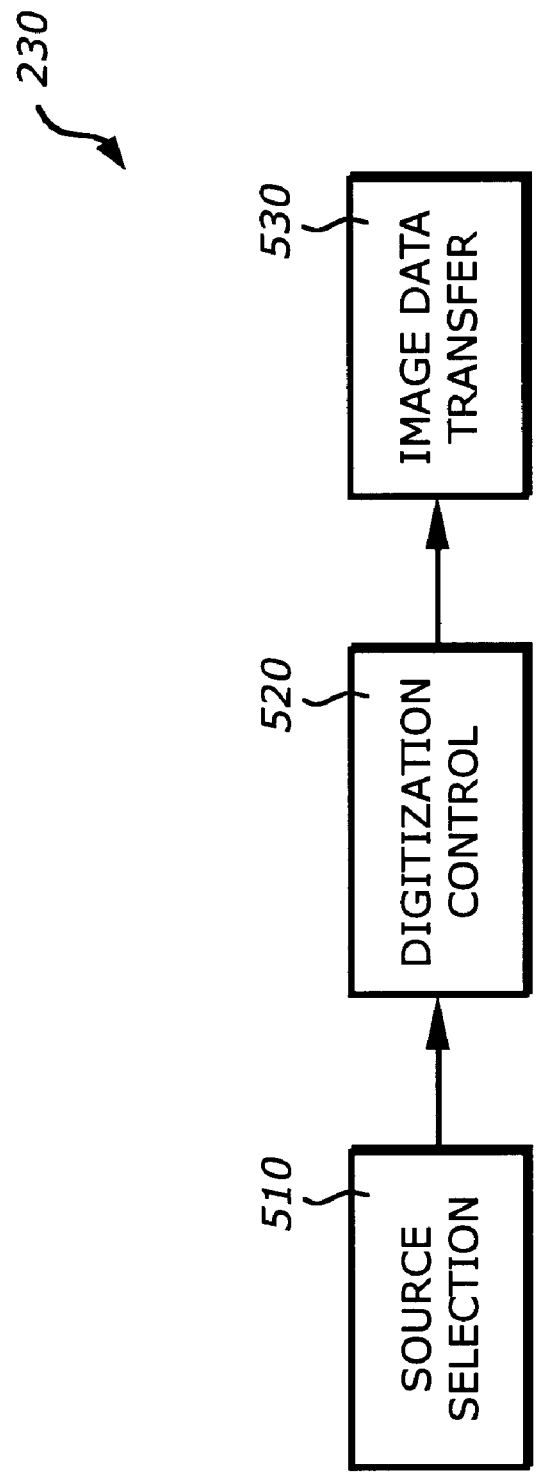
FIG. 5 is a diagram illustrating an image acquisition module according to one embodiment of the present invention.

FIG. 5 is a diagram illustrating an image acquisition module 240 according to one embodiment of the present invention. The image acquisition module 240 includes a source selection function 510, a digitization control function 520, and a image data transfer function 530.

Figure 6:
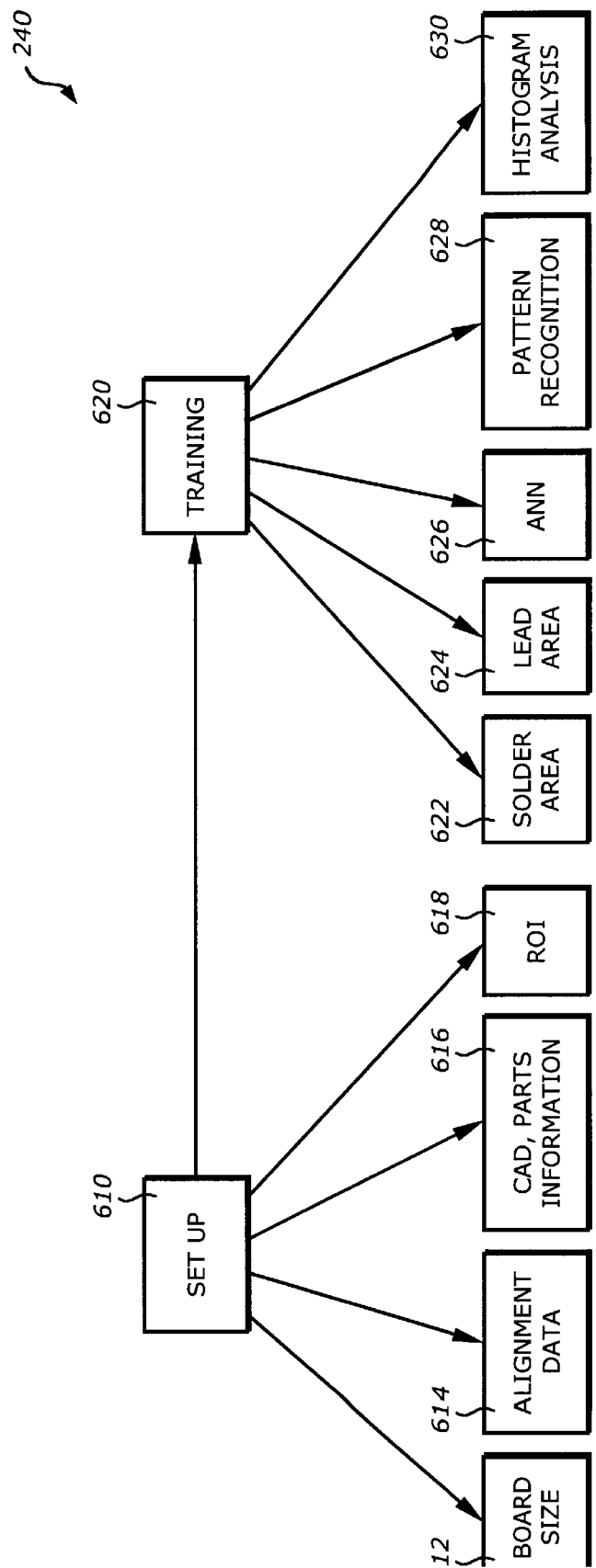
FIG. 6 is a diagram illustrating a training module according to one embodiment of the present invention.

The source selection function 510 controls the multiplexer to switch between the optical camera and the X-ray camera. The digitization control function 520 controls the frame grabber which captures the selected video signal from the camera. The image data transfer function 530 performs the transfer of digitized image data to and from the buffer memory, FIG. 6 is a diagram illustrating a training module 240 according to one embodiment of the present invention. The training module 240 includes a set-up function 610 and a training function 620.

The set-up function 610 prepares the system for generating the template for inspection. The set-up function allows the operator to enter set-up information such as a board size 612, an alignment data item 614, a CAD/parts information 616, and a region-of-interest (ROI) item 618. The board size 612 provides the dimensions of the board so that camera actions can be properly adjusted. In addition, the board size 612 is used to move the X-ray image assembly 125 and 145. The alignment data 614 provides landmark points on the board so that accurate registration can be made between the OUI 110 and a template from the database. The CAD/parts information 616 provides identification information for matching. The ROI 618 defines the position and size of the area to be inspected.

The training function 620 learns about the good board to compare with the OUI 110. The training function 620 includes a solder area training 622, a lead area training 624, an artificial neural network training 626, a pattern recognition (PR) training 628, and a histogram analysis 630.

The solder area training 622 allows training of the solder using a number of techniques. The use of multiple views from the positionable X-ray imaging assembly allows the examination of the solder at various viewing angles so that defective solder can be recognized. Another technique is to use controllable lighting to highlight the solder at different lighting intensities. The lead area training 624 allows training to detect solder bridge between the leads of an integrated circuit.

The ANN 626 learns the evaluation of the inspection by receiving information from a number of good boards. Examples of good solder joint images are shown to the ANN with corresponding classification. The ANN adjusts its own internal weights according to the training patterns to eventually generate correct classification. The PR training 628 performs template matching to determine a similarity measure between the OUI 110 and templates that are known to be good. The histogram analysis 630 compares the ratio of bright and dark pixels to the total number of pixels. Based on the lighting arrangement, defective solder joints typically provide different ratio than good solder joints.

FIG. 7 is a diagram illustrating an inspection module 250 according to one embodiment of the present invention. The inspection module 250 includes an alignment location function 710, a lead inspection 720, a solder inspection 730, and a template matching function 740.

The alignment location function 710 processes the image acquired by the image acquisition module 230 and extracts the landmark points as entered by the operator. The alignment location function 710 essentially performs image registration so that template matching between the OUI 110 and the template in the database can be made. The objective of the registration is to maintain correspondence between the two images. The registration can be performed by identifying landmark points on the board such as the fiducial marks or any other convenient points that are visible under both X-ray and direct visual imaging. Magnified images are properly scaled so that the dimensions of the X-ray image and the visual image are matched.

The lead inspection 720 utilize the training information from the lead area training 624 to inspect the lead area. The solder inspection 730 utilizes the training information from the solder area training 622 to inspect the solder area. The template matching 740 determines a similarity measure between the ROI of the OUI 110 and the corresponding region of the template of good board. This similarity measure is converted into inspection score.

FIG. 8 is a diagram illustrating a report generation module 260 according to one embodiment of the present invention. The report generation module 260 includes a result scoring function 810, a result summary function 820, and a result display function 830.

The result scoring function 810 produces an inspection score for the inspection of the OUI 110. The inspection score is typically a dimensionless number which is the quantitative measure of several inspection results. Examples of these inspection results include lead error, solder quality, parts identification code, part orientation. In one embodiment, the inspection score is a combination of the visual image inspection and the X-ray image inspection. The result summary function 820 produces a summary of the inspection including results of individual ROIs, of individual parts, and statistical results. The result display function 830 formats the result and displays on the display monitor.

Thus, the technique of the present invention provides a number of advantages for machine vision inspection. The imaging assembly is moved in X-Y directions so that defects visible in any viewing angle can be detected. The inspection also combines both the visual images and the X-ray images to detect defects visible in any of the imaging processes. In addition, a number of flexible features are incorporated to provide a robust and reliable inspection. These features include the neural network learning paradigm, the control of X-ray imaging assembly, the zooming of images, etc.

While this invention has been described with reference to illustrative embodiments, this description is not intended to be construed in a limiting sense. Various modifications of the illustrative embodiments, as well as other embodiments of the invention, which are apparent to persons skilled in the art to which the invention pertains are deemed to lie within the spirit and scope of the invention.

What is claimed is:

1. An apparatus for inspecting an object, the apparatus comprising:
    an inspection subsystem having therein, a holder holding an object to be inspected, an X-ray source, a first camera receiving an X-ray image of an object to be inspected and a second camera receiving a visible image of an object to be inspected, the X-ray source and first camera being positioned on opposite sides of the holder;
    an X-ray image processor coupled to the first camera receiving the X-ray image of the object to be inspected and processing the X-ray image data;
    a visual image processor coupled to the second camera receiving the visual image of the object to be inspected and processing the visual image data;
    a processing unit coupled to the visual image processor and X-ray image processor combining the results of the processing of the first and second images to generate a decision; and,
    a display for displaying the X-ray image and the visible image.

2. The apparatus of claim 1 wherein the first and second cameras are on the same side of the holder.

3. The apparatus of claim 1 wherein the X-ray source and the first camera are separately positionable relative to an object to be inspected to provide offset views of the features of the object to be inspected.

4. The apparatus of claim 1 wherein the first camera includes an X-ray camera.

5. The apparatus of claim 1 wherein the X-ray source and the first camera are positionable by translational movements.

6. The apparatus of claim 1 wherein the second camera is positionable by translational movements.

7. The apparatus of claim 1 wherein the object to be inspected is a printed circuit board containing electronic components, and the holder is a conveyor controlling the movement of the printed circuit board through the inspection area.

8. The apparatus of claim 7 wherein the X-ray source and the first camera are separately positionable relative to the printed circuit board to provide offset views of the printed circuit board to allow separation of the topside and the bottomside features of the printed circuit board.

9. The apparatus of claim 8 wherein the X-ray source and the first camera are positionable by X-Y movements.

10. The apparatus of claim 1 wherein the first and second cameras are moveable within the subsystem to controllably view different parts of the object to be inspected.

11. The apparatus of claim 1 wherein the visual image processor detects component presence and position, component identification, orientation and polarity, and/or solder defects.

12. The apparatus of claim 1 wherein the X-ray image processor detects voids, solder joint quality, and/or wire sweep measurement.

13. An apparatus for inspecting a printed circuit board with components thereon, the apparatus comprising:
    within a single inspection subsystem, a holder for holding a printed circuit board having first and second sides, an X-ray source on a first side of a printed circuit board in the holder, a first camera on the second side of a printed circuit board in the holder providing X-ray image data for a printed circuit board resulting from X-rays from the X-ray source passing through a printed circuit board and components thereon, and a second camera providing visible image data for one of the first and second sides of a printed circuit board in the holder;
    an X-ray image processor coupled to the first camera receiving the X-ray image data for the printed circuit board to be inspected and processing the X-ray image data;
    a visual image processor coupled to the second camera receiving the visual image data for the printed circuit board to be inspected and processing the visual image data;
    a processing unit coupled to the visual image processor and X-ray image processor combining the results of the processing of the visual image data and the X-ray image data to generate a decision.

14. The apparatus of claim 13 further comprised of a display for displaying the X-ray image data and the visible image data.

15. The apparatus of claim 13 wherein the first and second cameras are on the same side of the holder.

16. The apparatus of claim 13 wherein the X-ray source and the first camera are separately positionable relative to a printed circuit board in the holder to provide offset views of the features of the printed circuit board.

17. The apparatus of claim 13 wherein the first camera includes an X-ray camera.

18. The apparatus of claim 17 wherein the holder is a conveyor controlling the movement of a printed circuit board through the inspection area.

19. The apparatus of claim 18 wherein the X-ray source and the first camera are separately positionable relative to the printed circuit board to provide offset views of the printed circuit board to allow separation of the topside and the bottomside features of the printed circuit board.

20. The apparatus of claim 19 wherein the X-ray source and the first camera are positionable by X-Y movements.

21. The apparatus of claim 13 wherein the first and second cameras are moveable within the subsystem to controllably view different parts of the printed circuit board to be inspected.

22. The apparatus of claim 13 wherein the visual image processor detects component presence and position, component identification, orientation and polarity, and/or solder defects.

23. The apparatus of claim 13 wherein the X-ray image processor detects voids, solder joint quality, and/or wire sweep measurement.

24. A method for inspecting an object comprising:
    placing an object to be inspected into an inspection subsystem;
    passing X-ray radiation through the object to be inspected within the inspection subsystem;
    providing in electronic form X-ray image data of an object to be inspected within the inspection subsystem;
    providing in electronic form visual image data of an object to be inspected within the inspection subsystem;
    processing the visual image data to detect features in the visual image;
    processing the X-ray image data to detect features in the X-ray image; and,
    combining the results of the processing of the visual image data and the X-ray image data to generate a decision.

25. The method of claim 24 wherein the X-ray image data may include X-ray image data for X-ray radiation passing through the object to be inspected at different angles to provide offset views of the features of the object to be inspected.

26. The method of claim 24 wherein the object to be inspected is a printed circuit board containing electronic components, and the printed circuit board is placed in the inspection subsystem by a conveyor.

27. The method of claim 24 wherein providing in electronic form X-ray image data of an object to be inspected within the inspection subsystem is achieved by movement of a first camera to different positions within the inspection subsystem, and providing in electronic form visual image data of an object to be inspected within the inspection subsystem is achieved by movement of a second camera to different positions within the inspection subsystem.

28. The method of claim 26 wherein the visual image data is processed to detect component presence and position, component identification, orientation and polarity, and/or solder defects.

29. The method of claim 26 wherein the X-ray image data is processed to detect voids, solder joint quality, and/or wire sweep measurement.

30. The method of claim 24 wherein the X-ray image data may include X-ray image data for X-ray radiation passing through the printed circuit board and electronic components thereon at different angles to provide offset views of the topside and the bottomside features of the printed circuit board.

* * * * *